(12) United States Patent  (10) Patent No.: US 9,110,040 B2
Okada et al.  (45) Date of Patent: Aug. 18, 2015

(54) EXHAUST GAS MEASUREMENT DEVICE AND RECORDING MEDIUM HAVING PROGRAM FOR EXHAUST GAS MEASUREMENT DEVICE RECORDED THEREON

(71) Applicant: HORIBA, Ltd., Kyoto (JP)

(72) Inventors: Kaoru Okada, Kyoto (JP); Masayuki Hayata, Kyoto (JP); Toru Yamazaki, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 0 days.

(21) Appl. No.: 13/674,565

(22) Filed: Nov. 12, 2012

(65) Prior Publication Data

US 2013/0136656 A1    May 30, 2013

(30) Foreign Application Priority Data

Nov. 11, 2011  (JP) .................................. 2011-247098

(51) Int. Cl.
  *G01N 33/00*  (2006.01)
  *G01M 15/10*  (2006.01)
  *G06F 19/00*  (2011.01)
  *G01N 1/22*  (2006.01)
  *G01N 7/10*  (2006.01)
  *B01D 46/44* (2006.01)

(52) U.S. Cl.
  CPC ........ *G01N 33/0004* (2013.01); *G01N 33/0016* (2013.01); *B01D 46/446* (2013.01); *B01D 2279/30* (2013.01); *F01N 2560/00* (2013.01); *F01N 2560/02* (2013.01); *F01N 2560/05* (2013.01); *F01N 2560/08* (2013.01); *G01N 1/2247* (2013.01); *G01N 1/2252* (2013.01)

(58) Field of Classification Search
  USPC ....................................... 422/52, 83
  See application file for complete search history.

(56) References Cited

U.S. PATENT DOCUMENTS

| | | | | |
|---|---|---|---|---|
| 5,993,163 | A  * | 11/1999 | Iden ............................... | 417/43 |
| 2002/0178783 | A1* | 12/2002 | Miller et al. ................... | 73/23.2 |
| 2005/0060989 | A1* | 3/2005 | Kawashima et al. ........... | 60/295 |
| 2007/0251307 | A1 | 11/2007 | Graze, Jr. | |
| 2008/0067146 | A1* | 3/2008 | Onishi et al. .................... | 216/59 |
| 2010/0199839 | A1* | 8/2010 | Zhang et al. ...................... | 95/23 |
| 2012/0070757 | A1* | 3/2012 | Katano .......................... | 429/444 |
| 2013/0060485 | A1* | 3/2013 | Unger et al. .................... | 702/24 |

FOREIGN PATENT DOCUMENTS

| | | |
|---|---|---|
| JP | 08035918 | 2/1996 |
| JP | 08226878 | 9/1996 |
| JP | 09015139 | 1/1997 |

(Continued)

*Primary Examiner* — Jennifer Wecker
(74) *Attorney, Agent, or Firm* — Brooks Kushman P.C.

(57) ABSTRACT

An exhaust gas measurement device includes a pressure regulator for keeping a pressure of sample gas in a sensor flow line or a bypass flow line to be a set pressure value, a flow rate sensor provided on the bypass flow line for measuring a flow rate of the sample gas flowing through the bypass flow line, and an attention attracting part for displaying that the flow rate of the sample gas is reduced in the case where the flow rate measurement value measured by the flow rate sensor becomes equal to or smaller than an attention attracting flow rate value larger than a pressure controlling limit flow rate value by a predetermined value, the pressure controlling limit flow rate value being a lower limit flow rate value that is pressure-controllable by the pressure regulator.

6 Claims, 4 Drawing Sheets

(56) References Cited

FOREIGN PATENT DOCUMENTS

| | | | |
|---|---|---|---|
| JP | 2003-149099 A | | 5/2003 |
| JP | 2003149099 A | * | 5/2003 |
| JP | 2005049353 | | 2/2005 |
| JP | 2005127907 | | 5/2005 |
| JP | 2013524164 A | | 6/2013 |
| WO | WO2007121750 A1 | | 11/2007 |
| WO | WO 2011117115 A1 | * | 9/2011 |
| WO | WO2011117115 A1 | | 9/2011 |

* cited by examiner

EXHAUST GAS MEASUREMENT DEVICE AND RECORDING MEDIUM HAVING PROGRAM FOR EXHAUST GAS MEASUREMENT DEVICE RECORDED THEREON

CROSS-REFERENCE TO RELATED APPLICATION

This application claims priority to Japanese Application No. 2011-247098 filed Nov. 11, 2011, the disclosure of which is incorporated in its entirety by reference herein.

FIELD

The present invention relates to an exhaust gas measurement device for analyzing components contained in exhaust gas exhausted from such as, for example, an engine, and to a recording medium having a program for exhaust gas measurement device for use in the corresponding exhaust gas measurement device recorded thereon.

BACKGROUND

As an exhaust gas measurement device of this kind, there is one adapted to measure carbon monoxide (CO), total hydrocarbons (THC), nitrogen oxides ($NO_x$), carbon dioxide ($CO_2$) and the like contained, for example, in engine exhaust gas exhausted from an engine of an automobile (see Patent Literature 1).

Figure 4:
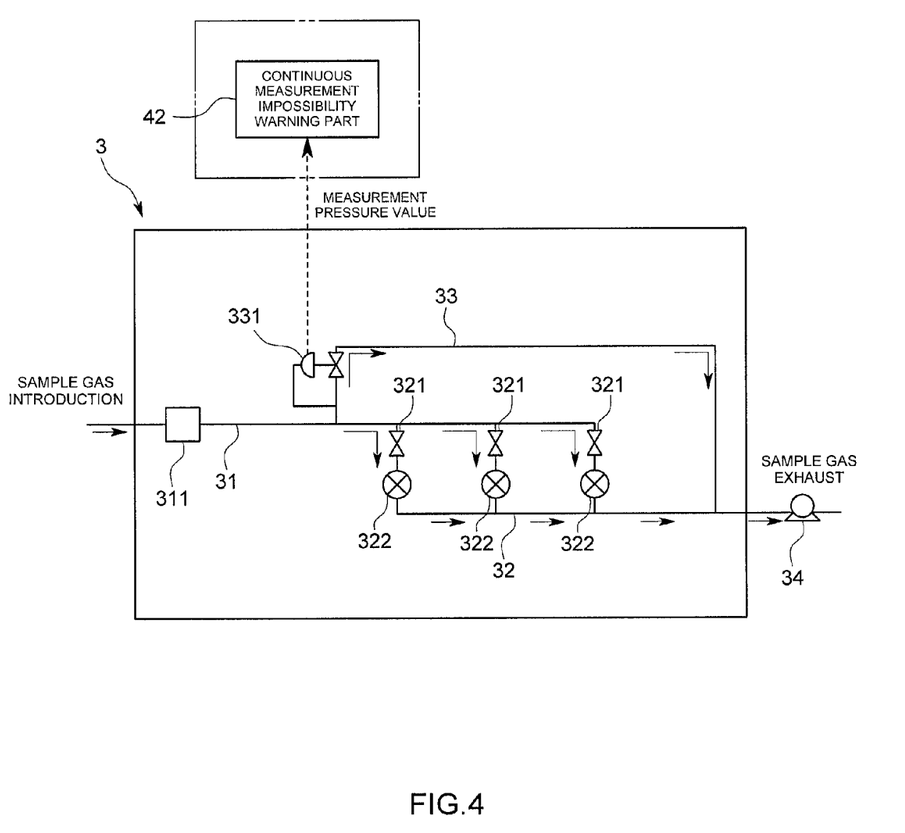
FIG. 4 is a schematic diagram showing a conventional exhaust gas measurement device.

Specifically referring to the exhaust gas measurement device, as shown in FIG. 4, this exhaust gas measurement device 3 includes two flow lines branched from an introduction flow line 31 to which sample gas containing exhaust gas is introduce, and one of the two flow lines is used as a sensor flow line 32 which is provided with a plurality of gas analyzers 322 for measuring various components and the other is used as a bypass flow line 33 which is configured to bypass the excessive sample gas which is unnecessary for the measurement. It is noted here that the phrase "to bypass the (excessive) sample gas" means "to guide the (excessive) sample gas to flow through the bypass flow line separated from the sensor flow line" in this description.

In this exhaust gas measurement device 3, in order to perform an accurate measurement in each of the gas analyzers 322, it is necessary to introduce sample gas into each of the gas analyzers 322 at a specific set pressure value. Therefore, it is configured such that the pressure thereof is to be kept at the set pressure value in a state that a predetermined quantity or more of the sample gas is rendered to flow through the bypass flow line 33 by a pressure regulator 331 provided on the bypass flow line 33. Further, the exhaust gas measurement device 3 is adapted to measure a pressure of the sample gas controlled by the pressure regulator 331 and provided with a continuous measurement impossibility display part 42 for displaying that the measurement of various components contained in the sample gas is not being performed accurately so that the measurement is impossible any more in a case where the measurement pressure value to be measured is largely apart from the set pressure value.

Then, a user, upon seeing that impossibility of the continuous measurement is displayed by the continuous measurement impossibility display part 42, checks, for example, a clogging of a filter 311 provided on the introduction flow line 31 and a pump for sucking the sample gas, which can be considered as a cause of the pressure control by the pressure regulator 331 being impossible, and after removing a cause of such a malfunction, the exhaust gas is to be measured again.

In this exhaust gas measurement device, however, a user can be informed of an abnormality of the exhaust gas measurement device only in the case where the filter is clogged or an ability of the pump is reduced to such a degree that the measurement of the exhaust gas cannot completely be continued. In other words, since the user is informed of an abnormality of the device only after such a large problem that the measurement of the exhaust gas cannot be continued occurs, the user cannot expect a time when the measurement becomes impossible in advance so that it cannot be helped to interrupt the measurement of the exhaust gas half-finished in some cases. Then, the measurement data interrupted in the middle of the measurement of the exhaust gas has to be abandoned due to such as a problem with continuation of a measurement condition and this may result in that the measurement of the exhaust gas then executed becomes useless.

SUMMARY

The present invention has been made in consideration of the above problems and has an object to provide an exhaust gas measurement device and a program for the exhaust gas measurement device which allow a user to expect a time when a pressure control executed by a pressure regulator becomes impossible and exhaust gas cannot be continuously measured and to perform maintenance of such as a filter and a pump before the measurement becomes completely impossible, so that interruption of the measurement during the measuring operation can be prevented.

That is, an exhaust gas measurement device of the present invention includes: an introduction flow line to which sample gas containing exhaust gas is introduced; a sensor flow line branched from the introduction flow line and provided with at least one gas analyzer for measuring components contained in the sample gas; a bypass flow line branched from the introduction flow line so as to bypass a part of the sample gas; a pressure regulator adapted to keep a pressure of the sample gas in the sensor flow line or the bypass flow line to be a set pressure value; a flow rate sensor provided on the bypass flow line and adapted to measure a flow rate of the sample gas flowing through the bypass flow line; and an attention attracting part adapted to display that the flow rate of the sample gas is reduced in the case where the flow rate measurement value measured by the flow rate sensor becomes equal to or smaller than an attention attracting flow rate value larger than a pressure controlling limit flow rate value by a predetermined value, the pressure controlling limit flow rate value being a lower limit flow rate value that is pressure-controllable by the pressure regulator.

In addition, a recording medium of the present invention has a program recorded thereon for use in an exhaust gas measurement device including: an introduction flow line to which sample gas containing exhaust gas is introduced; a sensor flow line branched from the introduction flow line and provided with at least one gas analyzer for measuring components contained in the sample gas; a bypass flow line branched from the introduction flow line so as to bypass a part of the sample gas; a pressure regulator adapted to keep a pressure of the sample gas in the sensor flow line or bypass flow line to be a set pressure value; and a flow rate sensor provided on the bypass flow line and adapted to measure a flow rate of the sample gas flowing through the bypass flow line. Herein the exhaust gas measurement device is provided with an attention attracting part adapted to display that the flow rate of the sample gas is reduced in the case where the flow rate measurement value measured by the flow rate sensor becomes equal to or smaller than an attention attracting flow rate value larger than a pressure controlling limit flow rate value by a predetermined value, the pressure controlling limit flow rate value being a lower limit flow rate value that is pressure-controllable by the pressure regulator.

With this configuration, instead of monitoring the pressure per se of the sample gas controlled by the pressure regulator so as to detect an abnormality such that the continuous measurement of the exhaust gas becomes impossible, it is configured that the attention attracting part detects an abnormality based on the measurement flow rate value measured by the flow rate sensor provided on the bypass flow line. Therefore, a user can be informed in advance that the continuous measurement of the exhaust gas will be impossible in the near future before the continuous measurement thereof actually becomes impossible, not a binary detection result as to whether or not there has occurred an abnormality of the continuous measurement of the exhaust gas being impossible.

More specifically, the attention attracting part is configured to display that the flow rate of the sample gas is reduced in the case where the flow rate measurement value measured by the flow rate sensor becomes equal to or smaller than an attention attracting flow rate value which is larger than a pressure controlling limit flow rate value by a predetermined value, wherein the pressure controlling limit flow rate value is a lower limit flow rate value that is pressure-controllable by the pressure regulator. Therefore, it becomes possible for a user to expect a time when the measurement of the exhaust gas becomes impossible during a measurement possible period of the exhaust gas. Thus, it becomes possible to perform maintenance of such as a filter and a pump, for example, at a time of outputting a display from the attention attracting part before the next measurement of the exhaust gas. Thus, it becomes possible to eliminate an accidental event such that the pressure control by the pressure regulator becomes impossible on the way of the measurement of the exhaust gas so that the measurement of the exhaust gas has to be interrupted on the way thereof and also prevent the measurement being uselessly abandoned.

The reason why it becomes possible for a user to expect a time when the continuous measurement of the exhaust gas becomes impossible in advance by monitoring the flow rate of the sample gas flowing in the bypass flow line not by monitoring a pressure of the sample gas, will be described here. In the case of monitoring a pressure of the sample gas, since the pressure is controlled by the pressure regulator to be constant at a set pressure value all the time, there arises no change in pressure so long as the filter is not completely clogged and it is difficult to inform the time when the measurement of the exhaust gas becomes impossible in advance. On the other hand, in the case of monitoring a flow rate of the sample gas, since the measurement flow rate value is gradually reduced in accordance with a degree of a clogging of the filter, a user can be attracted an attention of a time when the measurement of the exhaust gas becomes impossible before the measurement flow rate value becomes the pressure controlling limit flow rate value with which the pressure control cannot be performed. It should be noted that this specific feature of monitoring the measurement flow rate value is discovered by the present inventors as a result of their diligent studies and can be never easily found out.

In the case where a user ignores the display by the attention attracting part and continues the measurement of the exhaust gas and the like, in order to inform that an actual measurement value of each of the gas analyzers becomes an unreliable value so as to prevent the user from executing the measurement of the exhaust gas any more, the exhaust gas measurement device may preferably further include a warning part adapted to display that a pressure control by the pressure regulator is impossible in the case where the flow rate measurement value measured by the flow rate sensor becomes equal to or smaller than the pressure controlling limit flow rate value.

As another specific configuration for displaying by the warning part that the pressure control by the pressure regulator becomes impossible, there can be presented a configuration that the exhaust gas measurement device further includes a pressure sensor adapted to measure a pressure of the sample gas in the bypass flow line, wherein the warning part is configured to display that a pressure control by the pressure regulator is impossible in the case where a difference between the set pressure value and the measurement pressure value measured by the pressure sensor becomes equal to or larger than a predetermined value.

In order to explicitly indicate that the flow rate of the sample gas is yet within a range of allowing an accurate measurement of the exhaust gas in a state that the flow rate of the sample gas in the bypass flow line becomes equal to or smaller than the attention attracting flow rate value so as to prevent the user from erroneously interrupting the measurement of the exhaust gas, the attention attracting part may preferably be configured to display that the flow rate of the sample gas is reduced and display that the measurement by the gas analyzer is possible.

In order to explicitly indicate that the user cannot continue the measurement of the exhaust gas with an accurate value any more while ignoring the display by the attention attracting part and continuing the measurement of the exhaust gas so as to prevent the user from continuing an useless measurement, the warning part may preferably be configured to display that the pressure control by the pressure regulator is impossible and display that the measurement by the gas analyzer is also impossible.

As described above, according to the exhaust gas measurement device and the program for measuring the exhaust gas of the present invention, since the attention attracting part displays that the flow rate of the sample gas is reduced at the time when the flow rate of the sample gas flowing through the bypass flow line is reduced to the attention attracting flow rate value which is larger than the pressure controlling limit flow rate value, it becomes possible for a user to expect a time when the continuous measurement of the exhaust gas becomes impossible in advance before the measurement of the exhaust gas becomes completely impossible. Therefore, it is possible to perform maintenance of such as a filter and a pump in advance, so that it becomes possible to eliminate an accidental event such that the measurement of the exhaust gas has to be interrupted on the way.

REFERENCE SIGNS LIST

3 . . . Exhaust gas measurement device
31 . . . Introduction flow line

32 ... Sensor flow line
322 ... Gas analyzer
33 ... Bypass flow line
331 ... Pressure regulator
332 ... Flow rate sensor
41 ... Attention attracting part
42 ... Warning part

DETAILED DESCRIPTION

The following describes an exhaust gas measurement system 100 equipped with an exhaust gas measurement device 3 pertaining to the present invention with reference to the accompanying drawings.

Description of Entire Configuration

Figure 1:
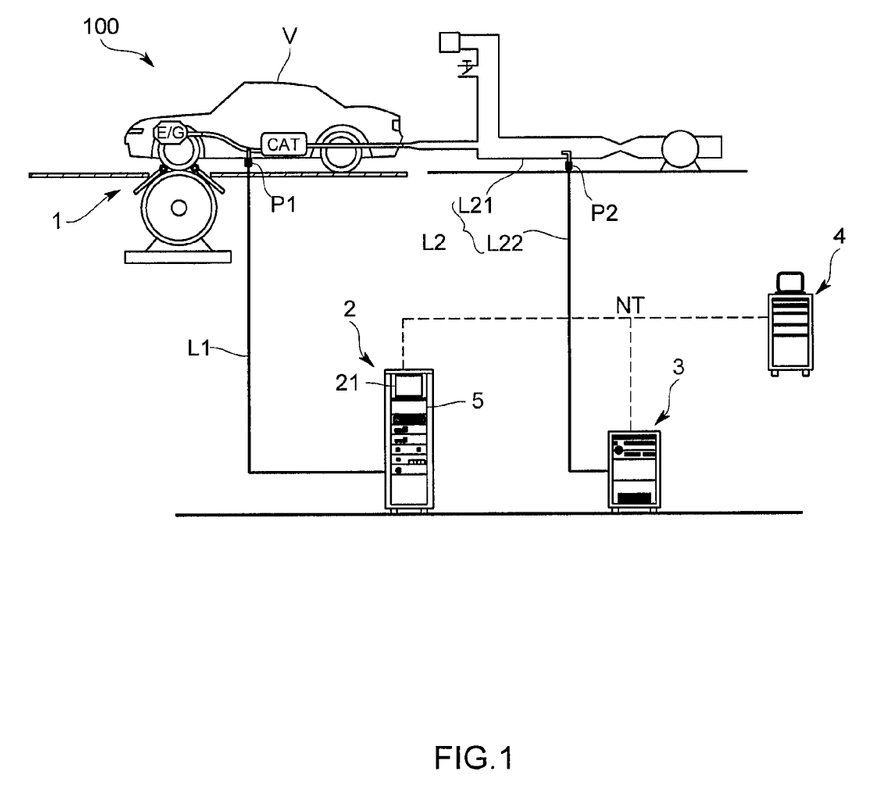
FIG. 1 is a schematic diagram showing an entire part of an exhaust gas measurement system pertaining to one embodiment of the present invention.

The exhaust gas measurement system 100 of the present embodiment is intended to perform an exhaust gas measurement of a vehicle V in a room referred to as a test cell and, as the entire configuration thereof shown in FIG. 1, the system 100 includes: a chassis dynamometer 1 on which the vehicle V that is a specimen in installed; first and second exhaust gas measurement devices 2 and 3 analyzing various components contained in the exhaust gas exhausted from an engine of the vehicle V; an exhaust gas flow line L leading the exhaust gas exhausted from the engine to the first and second exhaust gas measurement devices 2 and 3; and a central information processing unit 4 sending and receiving data between a dynamo control unit (not shown) controlling the chassis dynamometer 1 and each of the exhaust gas measurement devices 2 and 3. Also, the exhaust gas measurement system 100 includes an automatic drive mechanism installed at a driver's seat of a vehicle V and an automatic drive mechanism control unit for controlling the automatic drive mechanism (both of which are not shown), wherein the automatic drive mechanism is provided with a drive arm for mechanically driving an accelerator, brake, gear shift lever, handle and the like so that the vehicle V is automatically driven on the chassis dynamometer 1 by operating the drive arm based on an external control signal.

The exhaust gas flow line L includes: a first exhaust gas flow line L1 for leading engine exhaust gas exhausted from an engine to the first exhaust gas measurement device 2 without diluting the engine exhaust gas; and a second exhaust gas flow line L2 for diluting the engine exhaust gas through a dilution tunnel L21 and leading the diluted engine exhaust gas to the second exhaust gas measurement device 3, wherein the engine exhaust gas is discharged from the engine and passed through a catalyst (CAT) so as to be exhausted from an exhaust pipe (tail pipe).

The first exhaust gas flow line L1 includes an introduction port P1 having one end provided in an exhaust tube so that the engine exhaust gas discharged from the engine is introduced therein and the other end connected to a connection port (not shown) of the first exhaust gas measurement device 2 so that the first exhaust gas flow line L1 configures a direct sampling line for directly sampling the engine exhaust gas.

In addition, the second exhaust gas flow line L2 includes: the dilution tunnel L21 that is connected to the exhaust pipe of the vehicle V so as to dilute the engine exhaust gas with air; and a dilution sampling line L22 having an introduction port P2 with its one end provided in the dilution tunnel L21 so as to introduce the diluted exhaust gas and the other end connected to a connection port (not shown) of the second exhaust gas measurement device 3.

The first exhaust gas measurement device 2 is equipped with a plurality of gas analyzers having different measurement principles that are measuring instruments capable of continuously and individually measuring respective components such as CO, $CO_2$, $O_2$, HC, THC, $CH_4$, NO and $NO_x$ contained in the engine exhaust gas. For example, this first exhaust gas measurement device 2 includes: an infrared gas analyzer using a non-dispersive infrared (NDIR) absorption method for measuring concentrations of CO, $CO_2$, HC and NO; an $NO_x$ meter using a chemi-luminescence detection (CLD) method for measuring a concentration of $NO_x$; an $O_2$ meter using a magnetic pressure type detection (PMD) method for measuring a concentration of $O_2$; a THC meter using a heating-type flame ionization detection (HFID) method for measuring a concentration of THC and a $CH_4$ meter using a gas chromatography/hydrogen ionization detector (GC-FID) for measuring a concentration of $CH_4$. It noted here that THC is a pollution absorptive to the exhaust gas flow line L.

Herein, this first exhaust gas measurement device 2 is equipped with a computer system configured by using such as a CPU and a memory and has a function capable of mutually communicating such as a control signal and data with the outside.

The second exhaust gas measurement device 3 is equipped with a plurality of gas analyzers having different measurement principles that are measuring instruments capable of continuously and individually measuring respective components such as THC, $CH_4$ and NO contained in the diluted exhaust gas. For example, this second exhaust gas measurement device 3 includes: an infrared gas analyzer using a non-dispersive infrared (NDIR) absorption method for measuring a concentration of NO; a THC meter using a heating-type flame ionization detection (HFID) method for measuring a concentration of THC and a $CH_4$ meter using a gas chromatography/hydrogen ionization detector (GC-FID) for measuring a concentration of $CH_4$.

Herein, this second exhaust gas measurement device 3 is equipped with a computer system configured by using such as a CPU and a memory and has a function capable of mutually communicating such as a control signal and data with the outside.

The central information processing unit 4 is a computer system equipped with, for example, a CPU, a memory, a communication interface, a display, input means and the like and has a server function. Thus, the central information processing unit 4 is rendered to send and receive data to and from each of the various control units mentioned above and the first and second exhaust gas measurement devices 2 and 3 via a network NT such as a LAN so that it is allowed to execute a centralized control of the various control units and first and second exhaust gas measurement devices 2 and 3 and further execute data management.

Then, for example, by giving necessary parameters such as vehicle information and driving mode to the central information processing unit 4, the chassis dynamometer 1 and the automatic driving mechanism are centralizedly controlled via the control units thereof so that the vehicle V is driven in a desired manner and the first and second exhaust gas measurement devices 2 and 3 are operated to perform an automatic measurement of the exhaust gas data. Further, the exhaust gas data and driving data thereof are collectively managed in this central information processing unit 4.

It is noted here that the central information processing unit 4, each of the control units and the first and second exhaust gas measurement devices 2 and 3 are not necessarily separated in a physically independent distribution as shown in FIG. 1, and an aspect of partially or entirely integrating these components may be of course adoptable.

Details of Second Exhaust Gas Measurement Device 3

Next, the following describes the second exhaust gas measurement device 3 mentioned above in detail with reference to FIG. 2.

Figure 2:
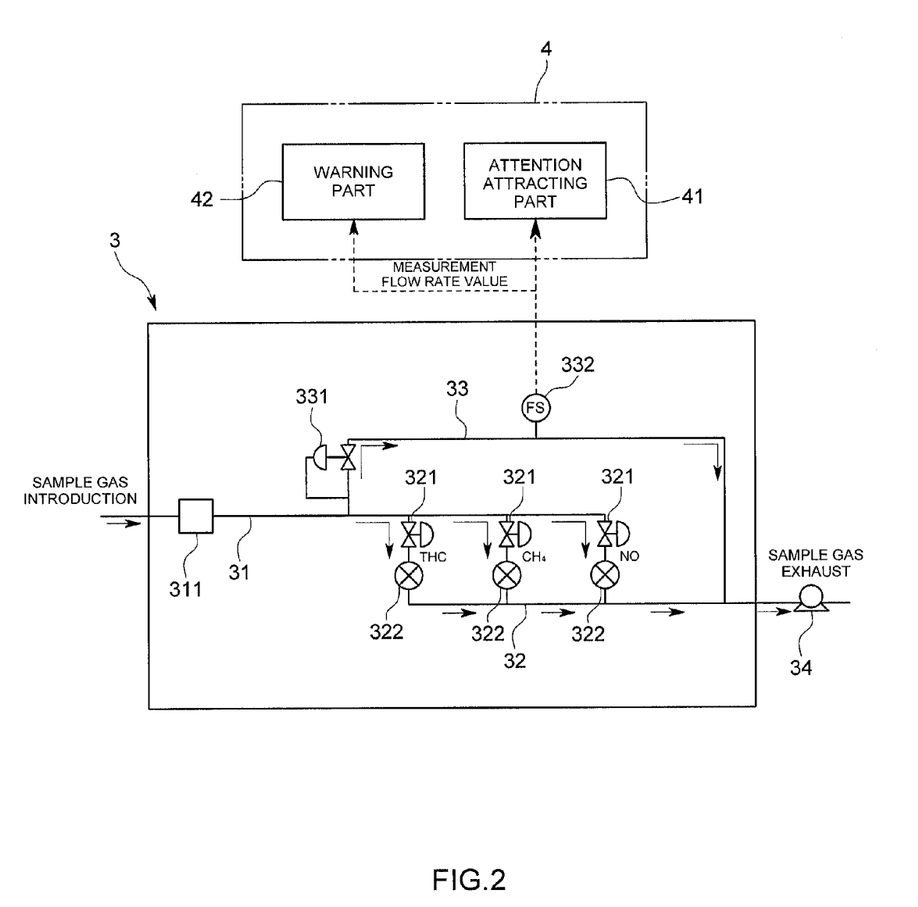
FIG. 2 is a schematic diagram showing details of an exhaust gas measurement device in the same embodiment.

The second exhaust gas measurement device 3 includes: an introduction flow line 31 to which sample gas containing exhaust gas is introduced; a sensor flow line 32 branched from the introduction flow line 31 and provided with at least one gas analyzer 322 for measuring components contained in the sample gas; and a bypass flow line 33 branched from the introduction flow line 31 so as to bypass a part of the sample gas. The sensor flow line 32 and the bypass flow line 33 are joined in a downstream and a suction pump 34 is provided in a downstream side of a confluence thereof for exerting a suction force in order to render the sample gas to flow in each of the flow lines. On the bypass flow line 33, there are provided a pressure regulator 331 for controlling a pressure of the sample gas and a flow rate sensor 332 for measuring a flow rate of the sample gas flowing through the bypass flow line 33. Further, the exhaust gas measurement device 3 includes an attention attracting part 41 adapted to display that the flow rate of the sample gas is reduced, based on the measurement flow rate value measured by the flow rate sensor 332 and further includes a warning part 42 adapted to display that a pressure control by the pressure regulator 331 is impossible, based on the measurement flow rate value.

Each part will be described below.

The introduction flow line 31 is a flow line to which exhaust gas diluted through the dilution tunnel 21 is introduced, and a filter 311 is provided midway thereof for removing such as particles contained in the exhaust gas.

The sensor flow line 32 is provided with the three gas analyzers 322 described above in parallel, i.e., an infrared gas analyzer for measuring a concentration of NO; a THC meter for measuring a concentration of THC; and a $CH_4$ meter for measuring a concentration of $CH_4$, and a flow rate control valve 321 is provided in an upstream side of each of the gas analyzers 321 for a flow rate necessary for measurement of each gas to flow into each of the gas analyzers 322. More specifically, it is configured that part of the sample gas introduced into the introduction flow line 31 is distributed at a predetermined ratio so that each of the distributed sample gas is rendered to flow into each of the gas analyzers 322.

The bypass flow line 33 is adapted to bypass a remaining flow rate by subtracting a flow rate of the sample gas flowing into the infrared gas analyzer, THC meter and $CH_4$ meter from a flow rate of the sample gas flowing into the introduction flow line 31 and the bypass flow line 33 is finally joined with the sensor flow line 32 so as to exhaust the bypassed flow rate. That is, the bypass flow line 33 is adapted to bypass an excessive flow rate unnecessary for the measurement of each of the gas analyzers 322 among the sample gas introduced into the introduction flow line 31. For example, the flow rate of the sample gas flowing through the bypass flow line 33 is kept to be 2.0 L/min under a normal condition.

The pressure regulator 331 is adapted to keep a pressure of the sample gas flowing through the sensor flow line 32 and the bypass flow line 33 to be constant at a predetermined set pressure value. The set pressure value is set to a pressure value needed to perform the measurement with an accurate value in each of the gas analyzers 322.

The flow rate sensor 332 is configured to measure the flow rate of the sample gas flowing through the bypass flow line 33 based on a pressure type or thermal type measurement principle so as to output a voltage value in accordance with the measurement flow rate value measured by the flow rate sensor 332. This outputted voltage value is retrieved in the central information processing unit 4 every predetermined sampling time so as to be sequentially displayed as time series data.

The attention attracting part 41 and the warning part 42 are configured to implement the functions thereof with the aid of a calculating function of the central information processing unit 4 and a display device.

The attention attracting part 41 is configured to display that the flow rate of the sample gas is reduced in the case where the flow rate measurement value measured by the flow rate sensor 332 becomes equal to or smaller than an attention attracting flow rate value which is larger than a pressure controlling limit flow rate value by a predetermined value, wherein the pressure controlling limit flow rate value is a lower limit flow rate value that is pressure-controllable by the pressure regulator 331.

The warning part 42 is configured to display that a pressure control by the pressure regulator 331 is impossible in the case where the flow rate measurement value measured by the flow rate sensor 332 becomes equal to or smaller than the pressure controlling limit flow rate value.

Description of Operation of Attention Attracting Part 41 and Warning Part 42

The following describes the operations of the attention attracting part 41 and the warning part 42 of the second exhaust gas measurement device 2 configured as described above with reference to a graph in FIG. 3.

Figure 3:
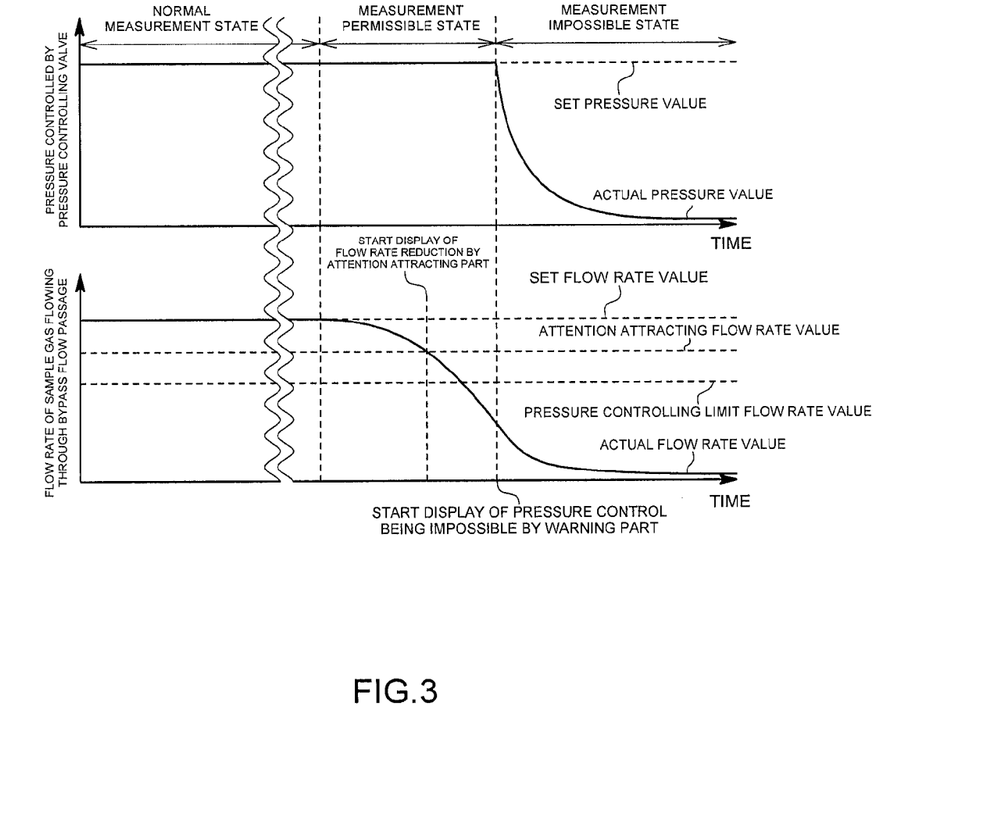
FIG. 3 is a schematic graph view showing operation timings of an attention attracting part and a warning part in the same embodiment.

As shown in FIG. 3, in a normal measurement state, i.e., an initial measurement state where there occurs no clogging in the filter 311 and there occurs no problem also in the suction pump 34, the pressure of the sample gas controlled by the pressure regulator 331 is kept constant at the set pressure value and the measurement flow rate value measured by the flow rate sensor 332 is also kept constant at the set flow rate value.

In the case where a clogging begins to occur in the filter 311 or a performance of the suction pump 34 begins to be reduced due to such as adhesion of the exhaust gas components with time lapse, the operation is brought in a measurement permissible state where the pressure of the sample gas is kept constant at the set pressure value by the pressure regulator 331 while the measurement flow rate value measured by the flow rate sensor 332 is gradually reduced. The reason why such a state occurs is because, even though an amount of the sample gas introduced into the introduction flow line 31 is reduced due to such as a clogging of the filter 311, the pressure control by the pressure regulator 331 can be performed before the introduced flow rate value becomes the pressure controlling limit flow rate value. That is, the measurement permissible state can also be referred to a state where since there does not occur such as a clogging in the filter 311 in a critical degree, the measurement by each of the gas analyzers 322 can be performed with a prescribed accuracy although an abnormality such as a clogging begins to occur. In this measurement permissible state, when the flow rate value becomes the attention attracting flow rate value which is larger than the pressure controlling limit flow rate value by a predetermined value, the attention attracting part 41 displays that the flow rate of the sample gas is reduced.

With further time lapse, the measurement flow rate value measured by the flow rate sensor 332 becomes equal to or smaller than the pressure controlling limit flow rate value, and at this point and thereafter, the operation is brought in a measurement impossible state where the pressure of the sample gas is varied to a value different from the set pressure. In this state, since the pressure of the sample gas cannot be kept constant at the set pressure value by the pressure regulator 331, the measurement value outputted by each of the gas analyzers 322 does not satisfy the measurement condition and an inaccurate value is accordingly outputted. At the time of the measurement flow rate value of the flow rate sensor 332 being equal to or smaller than the pressure controlling limit flow rate value, the warning part 42 detects the state to be the measurement impossible state and displays that the pressure control by the pressure regulator 331 is impossible.

For example, assuming that the flow rate of the sample gas flowing through the bypass flow line 33 under the normal measurement condition is 2.0 L/min, the pressure controlling limit flow rate value becomes about 0.7 L/min. Therefore, the attention attracting flow rate value is set within a range of 2.0 to 0.7 L/min. The attention attracting flow rate value is set so as to prevent the state from becoming the measurement impossible state immediately after starting an attention attraction, in consideration of such as a time elapsed until the measurement of the exhaust gas is finished.

Effect of the Present Embodiment

According to the exhaust gas measurement system 100 and exhaust gas measurement devices 2 and 3 configured as described above, since it is configured such that the flow rate of the sample gas flowing through the bypass flow line 33 is monitored and at a time when the measurement flow rate value thereof becomes the attention attracting flow rate value which is larger than the pressure controlling limit flow rate value, it is displayed that the flow rate of the sample gas is reduced without stopping the gas measurements, therefore it becomes possible for a user to expect a time when the measurement becomes impossible before the pressure cannot be kept constant and the accurate measurement executed by each of the gas analyzers 322 becomes impossible. Therefore, the user can perform such as maintenance in advance before the exhaust gas measurement device 3 becomes completely impossible to perform the measurement due to such as a clogging of the filter 311 and reduction in performance of the suction pump 34, so that it becomes possible to eliminate an accidental event such that the measurement of the exhaust gas has to be interrupted on the way. That is, in the case where the monitoring is performed based on the pressure of the sample gas as in the conventional method, although there arises a problem that a user can be informed only when the measurement of the exhaust gas becomes completely impossible so that the measurement of the exhaust gas is interrupted on the way and the measurement data has been useless, such a conventional problem can be eliminated by the present embodiment.

Other embodiments will be described below.

In the above embodiments, although the attention attracting part is adapted to display the reduction of the flow rate of the sample gas, it may be further displayed that the measurement by the gas analyzer is possible. In addition, although the warning part is adapted to display that the pressure control by the pressure regulator is impossible, it may be further displayed that the measurement by the gas analyzer is also impossible. In addition, although the warning part is configured to determine whether or not the pressure control by the pressure regulator is impossible based on the measurement flow rate value, it may be configured that the pressure per se of the sample gas is monitored and in the case where the pressure value becomes a value apart from the set pressure value by a predetermined value or more, it is displayed that the pressure control is impossible.

In the above embodiments, although an example applying the present invention to the second exhaust gas measurement device is shown, a similar configuration may be applied to the first exhaust gas measurement device. Moreover, in the above embodiments, although the functions of the attention attracting part and the warning part are implemented by the central information processing unit, the functions may be implemented with use of, for example, a calculation function of the first exhaust gas measurement device or the second exhaust gas measurement device and a display device. In addition, the flow rate sensor may be provided on a flow line other than the bypass flow line, e.g., on the introduction flow line or the sensor flow line. However, it is more preferable to provide the flow rate sensor on the bypass flow line because in that case the flow rate sensor is unlikely to have a bad effect on a measurement accuracy of each of the gas analyzers.

Further, a program for the exhaust gas measurement device for implementing the function of the attention attracting part may be installed in the computer constituting the existing exhaust gas measurement device by a recording medium and the like.

In addition, the present invention should not be limited by the present embodiment, and various modifications or combination of the embodiments may be made within the scope unless departing from the intended spirit thereof.

INDUSTRIAL APPLICABILITY

By utilizing the present invention, since the reduction of the flow rate is displayed at the time when the flow rate of the sample gas flowing through the bypass flow line is reduced to the attention attracting flow rate value which is larger than the pressure controlling limit flow rate value, it becomes possible for a user to expect a time when the continuous measurement of the exhaust gas becomes impossible before the measurement of the exhaust gas becomes completely impossible. Therefore, it is possible to provide an exhaust gas measurement device capable of performing maintenance of such as a filter and a pump in advance, so that it becomes possible to eliminate an accidental event such that the measurement of the exhaust gas has to be interrupted on the way.

The invention claimed is:

1. An exhaust gas measurement device comprising:
   an introduction flow line to which sample gas containing exhaust gas is introduced;
   a sensor flow line branched from the introduction flow line and provided with at least one gas analyzer configured for continuous measurement of components contained in the sample gas;
   a bypass flow line branched from the introduction flow line so as to bypass a part of the sample gas;
   a flow rate sensor provided on the bypass flow line and adapted to measure a flow rate of the sample gas flowing through the bypass flow line;
   a pressure regulator adapted to keep a pressure of the sample gas in the sensor flow line or the bypass flow line to be a set pressure value provided the flow rate is greater than a pressure controlling limit flow rate value; and
   an attention attracting part programmed to display that the flow rate is reduced in the case where a flow rate measurement value of the sample gas measured by the flow rate sensor becomes equal to or less than an attention attracting flow rate value to provide a user an advanced warning that the continuous measurement will be interrupted and become impossible, the attention attracting flow rate value being greater than the pressure controlling limit flow rate value, and the at least one gas analyzer being programmed to continue the continuous measurement after the flow rate measurement value of the sample gas measured by the flow rate sensor becomes equal to or less than the attention attracting flow rate value.

2. The exhaust gas measurement device according to claim 1 further comprising a warning part programmed to display that a pressure control by the pressure regulator is impossible in the case where the flow rate measurement value measured by the flow rate sensor becomes equal to or less than the pressure controlling limit flow rate value.

3. The exhaust gas measurement device according to claim 2 further comprising a pressure sensor adapted to measure a pressure of the sample gas in the bypass flow line, wherein
the warning part is configured to display that a pressure control by the pressure regulator is impossible in the case where a difference between the set pressure value and the measurement pressure value measured by the pressure sensor becomes equal to or greater than a predetermined value.

4. The exhaust gas measurement device according to claim 1, wherein the attention attracting part is configured to display that the flow rate of the sample gas is reduced and display that the measurement by the gas analyzer is possible.

5. The exhaust gas measurement device according to claim 2, wherein the warning part is configured to display that the pressure control by the pressure regulator is impossible and display that the measurement by the gas analyzer is also impossible.

6. A recording medium having a program recorded thereon that, when executed by an exhaust gas measurement device comprising an introduction flow line to which sample gas containing exhaust gas is introduced, a sensor flow line branched from the introduction flow line and provided with at least one gas analyzer configured for continuous measurement of components contained in the sample gas, a bypass flow line branched from the introduction flow line so as to bypass a part of the sample gas, a flow rate sensor provided on the bypass flow line and adapted to measure a flow rate of the sample gas flowing through the bypass flow line, and a pressure regulator adapted to keep a pressure of the sample gas in the sensor flow line or the bypass flow line to be a set pressure value provided the flow rate is greater than a pressure controlling limit flow rate value,
causes an attention attracting part of the exhaust gas measurement device to display that the flow rate is reduced in the case where a flow rate measurement value of the sample gas measured by the flow rate sensor becomes equal to or less than an attention attracting flow rate value to provide a user an advanced warning that the continuous measurement will be interrupted and become impossible, the attention attracting flow rate value being greater than the pressure controlling limit flow rate value, and
causes the at least one gas analyzer to continue the continuous measurement after the flow rate measurement value of the sample gas measured by the flow rate sensor becomes equal to or less than the attention attracting flow rate value.

* * * * *